(12) United States Patent
Keller

(10) Patent No.: US 6,876,322 B2
(45) Date of Patent: Apr. 5, 2005

(54) CONCEALED OBJECT DETECTION

(75) Inventor: Paul E. Keller, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/607,552

(22) Filed: Jun. 26, 2003

(65) Prior Publication Data

US 2004/0263379 A1 Dec. 30, 2004

(51) Int. Cl.[7] ............................. G01S 13/00; G03H 3/00
(52) U.S. Cl. ............................. 342/22; 342/179; 367/8
(58) Field of Search .................... 342/22, 179; 367/8

(56) References Cited

U.S. PATENT DOCUMENTS

| | | | |
|---|---|---|---|
| 3,689,772 A | | 9/1972 | George et al. |
| 5,073,782 A | | 12/1991 | Huguenin et al. |
| 5,081,456 A | * | 1/1992 | Michiguchi et al. .......... 342/22 |
| 5,227,800 A | | 7/1993 | Huguenin et al. |
| 5,274,714 A | | 12/1993 | Hutcheson et al. |
| 5,367,552 A | | 11/1994 | Peschmann |
| 5,455,590 A | * | 10/1995 | Collins et al. .............. 342/179 |
| 5,557,283 A | | 9/1996 | Sheen et al. |
| 5,600,303 A | | 2/1997 | Husseiny et al. |
| 5,857,030 A | | 1/1999 | Gaborski et al. |
| 5,859,609 A | | 1/1999 | Sheen et al. |
| 5,963,667 A | | 10/1999 | Hashimoto et al. |
| 6,018,562 A | | 1/2000 | Wilson |
| 6,038,337 A | | 3/2000 | Lawrence et al. |
| 6,057,761 A | | 5/2000 | Yukl |
| 6,081,750 A | | 6/2000 | Hoffberg et al. |
| 6,324,532 B1 | | 11/2001 | Spence et al. |
| 6,359,582 B1 | | 3/2002 | MacAleese et al. |
| 6,418,424 B1 | | 7/2002 | Hoffberg et al. |
| 6,480,141 B1 | | 11/2002 | Toth et al. |
| 6,507,309 B2 | | 1/2003 | McMakin et al. |
| 6,700,526 B2 | * | 3/2004 | Witten .......................... 342/22 |
| 2003/0034444 A1 | | 2/2003 | Chadwick et al. |
| 2003/0053698 A1 | | 3/2003 | Ferguson |
| 2003/0086525 A1 | | 5/2003 | Rhee et al. |
| 2003/0117310 A1 | | 6/2003 | Kikuchi et al. |
| 2003/0163042 A1 | | 8/2003 | Salmon |
| 2003/0179126 A1 | | 9/2003 | Jablonski et al. |

FOREIGN PATENT DOCUMENTS

WO     WO 02/17231 A2     2/2002

* cited by examiner

*Primary Examiner*—Thomas H. Tarcza
*Assistant Examiner*—Brian Andrea
(74) *Attorney, Agent, or Firm*—Woodard, Emhardt, Moriarty, McNett & Henry LLP

(57) ABSTRACT

Disclosed are systems, methods, devices, and apparatus to interrogate a clothed individual with electromagnetic radiation to determine if a concealed weapon is being carried. This determination includes establishing data corresponding to an image of the individual and processing data sets corresponding to a number of spatial frequency representations of different image portions to evaluate if the concealed weapon is present.

39 Claims, 13 Drawing Sheets

Fig. 7

CONCEALED OBJECT DETECTION

BACKGROUND

The present invention relates to detection of concealed objects, and more particularly, but not exclusively relates to detecting weapons or contraband carried by a person beneath clothing.

The detection of weapons, contraband, and other concealed objects is of significant interest at security checkpoints and the like. One approach utilizes a magnetometer to detect certain metallic objects. Unfortunately, this approach does not detect most organic polymer and composite materials that may be used to fabricate firearms, explosives, and other objects which are frequently the subject of security inspections.

In another approach, millimeter wave electromagnetic radiation is applied to provide images that can reveal objects concealed by clothing. This approach typically depends on the ability of a human inspector to visually detect one or more suspect objects from the resulting image. Accordingly, there are intrinsic speed limitations in these approaches, and such approaches are subject to variation with the ability of different inspectors. Moreover, because these systems can provide detailed images of body parts that are ordinarily intended to be hidden by clothing, utilization of a human inspector can be embarrassing to the person being inspected, and may pose a concern that privacy rights are being violated. Thus, there is an on going demand for further contributions in this area of technology.

SUMMARY OF INVENTION

One embodiment of the present invention is a unique technique to detect objects. Other embodiments include unique systems, devices, methods, and apparatus to determine if a person is carrying a concealed man-made object.

A further embodiment of the present invention includes a technique to scan a clothed person with electromagnetic radiation and determine if a man-made object is being carried by the person beneath their clothing. This determination can be made by analysis of image data from the scan with one or more processors to identify one or more image regions suspected of revealing a concealed man-made object. These regions can then be displayed for verification by a human inspector. As a result, only those portions of an image suspected of revealing concealed objects are subject to human inspection. Optionally, the processor analysis can be arranged to discriminate between different types of man-made objects. In one form, analysis focuses on the detection of weapons or contraband. As used herein, a weapon includes, but is not limited to, a knife, firearm, gun, explosive, bomb, incendiary device, gas or particle dispensing device, or any portion thereof. Alternatively or additionally, a different type of man-made object may be the subject of detection in other forms of such embodiments.

In another embodiment, a person is irradiated by electromagnetic radiation within a frequency range of about 200 Megahertz (MHz) to about 1 Tetrahertz (THz). Data representative of an image of the person is established from the irradiation and several data sets are determined from this data. The data sets each correspond to a spatial frequency representation of a different portion of the image. The data sets are adaptively processed to identify a man-made object being carried by the person. In one form, the data set determination includes performing a Fourier transform operation with different portions of the data to provide respective spatial frequency data representations, and applying an image feature extraction filter to each of the spatial frequency data representations to correspondingly provide the data sets for adaptive processing.

Still another embodiment of the present invention includes: establishing data corresponding to an image of a concealed surface by irradiating with electromagnetic radiation including one or more frequencies in a range of about 200 MHz to about 1 THz, generating a data set corresponding to a spatial frequency representation of at least a portion of the image from the data, and identifying a concealed man-made object by analyzing the data with a neural network. In one form, the data can be established by performing a scan of a person in a portal at a security check point with the electromagnetic radiation, and the concealed man-made object is at least one of a weapon and contraband.

Yet another embodiment includes: irradiating a person at least partially covered with clothing, detecting electromagnetic radiation reflected from a surface beneath the clothing in response, establishing data corresponding to a spatial frequency representation of the surface from the radiation, and analyzing the data with a neural network to identify a man-made object being carried by the person beneath the clothing.

A further embodiment of the present invention includes irradiating a person at least partially covered by clothing with electromagnetic radiation including one or more frequencies in a range of 200 MHz to about 1 THz, and in response, establishing data representative of an image of the person that may include details of one or more body parts that are normally hidden by the clothing. Several data sets are determined each corresponding to a respective one of a number of different image portions that are numerically processed relative to one or more criteria to evaluate if one or more of the different image portions reveals a man-made object beneath the clothing. If the one or more criteria are satisfied, an image of the man-made object is displayed relative to a location on the person. Accordingly, if these one or more criteria are not satisfied, then an image of the person need not be displayed. Indeed, even when an image is displayed, it can be limited to a region proximate to its location on the person's body and/or can be shown relative to a gender-neutral representation of the person, such as a silhouette, wire-frame outline, mannequin, or the like.

Another embodiment of the present invention includes a system with a sensing array operable to interrogate a person with electromagnetic radiation and one or more processors operable to establish data representative of an image of the person from one or more input signals provided by the array. The one or more processors are operable to generate a number of data sets each corresponding to a spatial frequency representation of a different portion of the image from the data and analyze the data sets with a neural network to detect if the person is carrying a man-made object.

In still another embodiment, an apparatus includes a device carrying logic executable by one or more processors to process data corresponding to an image of a person obtained from electromagnetic radiation including one or more frequencies in a range of about 200 MHz to about 1 THz. The logic is further operable to generate a number of data sets each corresponding to a spatial frequency representation of a respective one of a number of different portions of the image and adaptively process each of these data sets relative to one or more criteria to determine if one or more of the different portions of the image show an object. The logic provides signals to display at least a portion of the object relative to a location on the person if the one or more criteria are satisfied. In one form, the logic is further operable to perform a Fourier transform operation with different portions of the data to correspondingly provide a number of sets of spatial frequency data, and apply an image feature filter to each of the sets of spatial frequency data to correspondingly provide the data sets for adaptive processing. In another form, the logic alternatively or additionally defines a neural network to perform the adaptive processing of the data sets.

Accordingly, one object of the present invention is to provide a unique technique to detect objects, weapons, and/or contraband.

Another object is to provide a unique system, method, or apparatus to determine if a person is carrying a concealed device, object, or material of interest.

Other objects, embodiments, forms, features, advantages, aspects and benefits of the present invention shall become apparent from the detailed description and drawings included herein.

BRIEF DESCRIPTION OF THE DRAWINGS

FIG. 7 is a diagram illustrating segmentation of an image into overlapping rectangular portions for use in the procedure of FIGS. 3–5.

DETAILED DESCRIPTION

Figure 1:
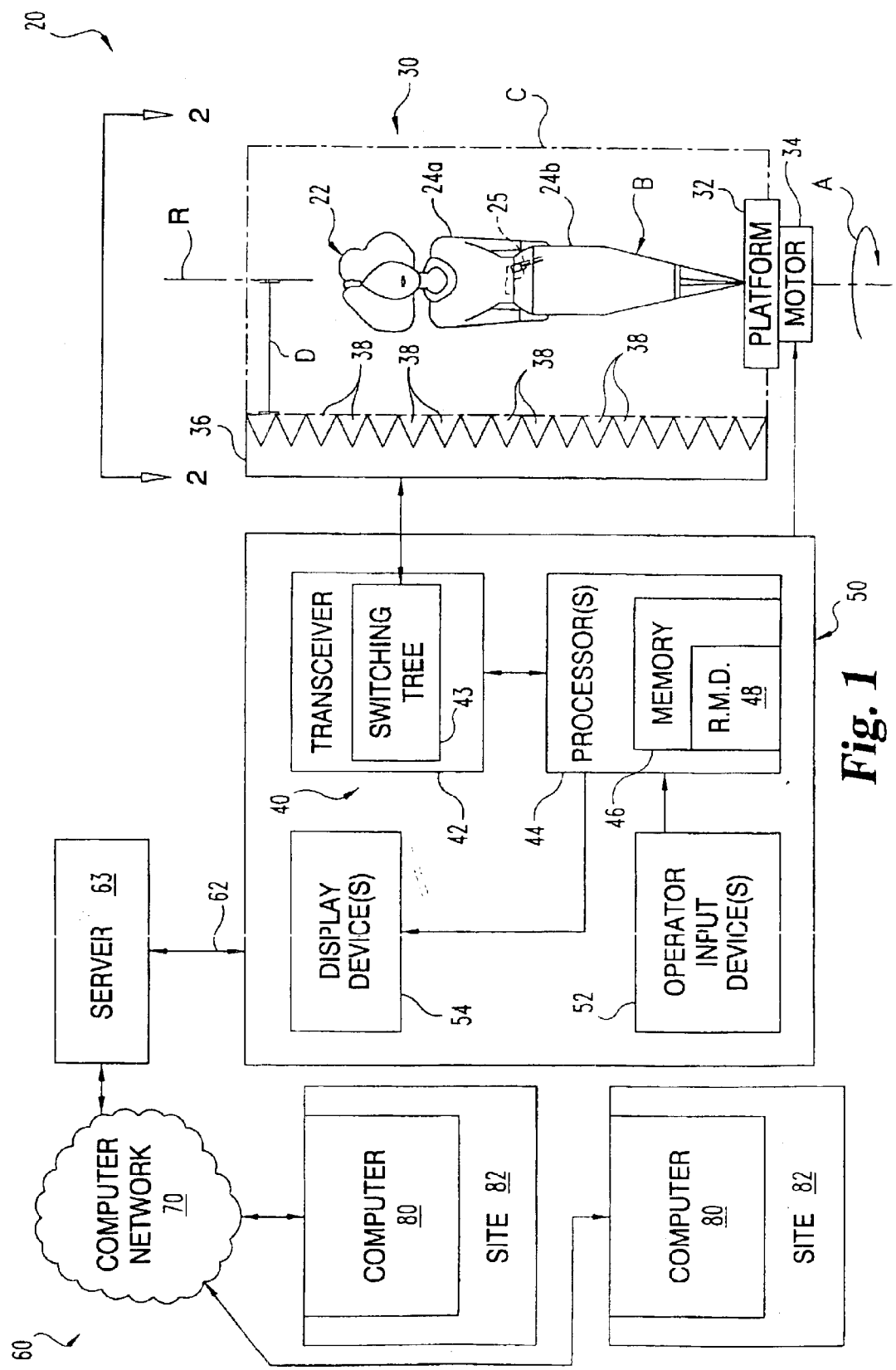
FIG. 1 is a partial, diagrammatic view of a security inspection system.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates security inspection system 20 of one embodiment of the present invention. In operation, system 20 interrogates an animate or inanimate object by illuminating it with electromagnetic radiation in the 200 Megahertz (MHz) to 1 Terahertz (THz) frequency range and detecting the reflected radiation. Generally, the corresponding wavelengths range from several centimeters to a few micrometers. Certain natural and synthetic fibers are often transparent or semi-transparent to such frequencies/wavelengths, permitting the detection and/or imaging of surfaces positioned beneath such materials. When the subject of interrogation is a clothed individual, image information about portions of a person's body covered by clothing or garments can typically be obtained with system 20, as well as those portions that are not covered by clothing or garments. Further, image information relative to objects carried by a person beneath clothing can be provided with system 20 for metal and non-metal object compositions commonly used for weapons and contraband.

As illustrated in FIG. 1, body B is in the form of a person 22 presented for interrogation by system 20. Person 22 is portrayed in a typical manner, being at least partially covered by garments or clothing designated more specifically by reference numerals 24a and 24b. Clothing items 24a and 24b conceal object 25 shown in the form of a weapon in phantom. Person 22 is positioned in scanning/illumination portal 30 of system 20. Portal 30 is configured for placement at a security checkpoint of the type where it is desired to detect weapons and/or contraband. Portal 30 includes platform 32 connected to motor 34. Platform 32 is arranged to support person 22 or such other object desired to be examined with system 20. Motor 34 is arranged to selectively rotate about rotational axis R while person 22 is positioned thereon. For the orientation shown, axis R is approximately vertical, and person 22 is in a generally central position relative to axis R and platform 32. In one form, platform 32 can be comprised of a material, such as an organic thermoplastic or thermoset polymer, that permits the interrogation in or beneath the soles of shoes where weapons can sometimes be hidden.

Figure 2:
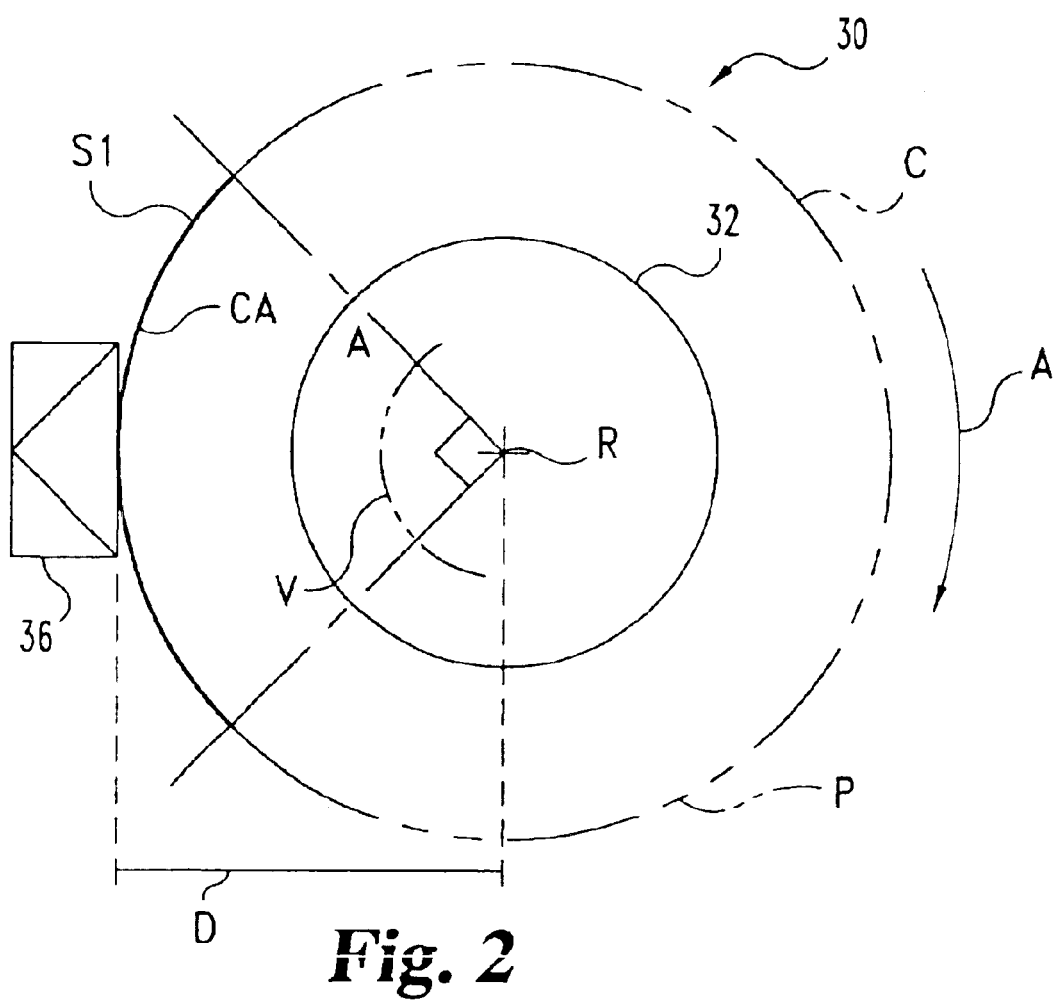
FIG. 2 is a partial, top view of the FIG. 1 system along the view line 2—2 shown in FIG. 1.

Portal 30 further includes multiple element-sensing array 36. Referring additionally to the partial top view of FIG. 2, the relationship of platform 32 to array 36 is further illustrated. Axis R is generally perpendicular to the view plane of FIG. 2 and is represented by crosshairs. As motor 34 causes platform 32 to rotate about axis R, array 36 circumscribes a generally circular pathway P about axis R. Circular pathway P corresponds to an imaginary cylinder C with radius D. Radius D is the distance from axis R to array 36. In one preferred form, radius D is about 0.5 to about 2 meters. In a more preferred form, radius D is about 0.5 meters to 1.5 meters—corresponding to about a 1 meter to 3 meter diameter. Arrow A shown in FIGS. 1 and 2 represents the selective rotation of platform 32 about axis R.

Sensing array 36 includes a number of linearly arranged elements 38 only a few of which are schematically illustrated and specifically designed by reference numerals to preserve clarity. Elements 38 each operate to transmit or receive electromagnetic radiation within a selected bandwidth. Sensing array 36 is coupled to processing subsystem 40. Subsystem 40 includes transceiver 42 with switching tree 43 coupled to elements 38 of array 36. In one form, the position of array 36 relative to platform 32 is determined with one or more positional encoders (not shown) that are coupled to subsystem 40. In other forms, one or more different position tracking devices and/or techniques can be used.

Under the control of transceiver 42, individual elements 38 can be selectively activated with switching tree 43. Each element 38 is dedicated to transmission or reception. Elements 38 are arranged in two generally vertical columns arranged in a generally back-to-back relationship with one another. Elements 38 comprising one of the columns are dedicated to transmission and elements 38 comprising the other of the columns are dedicated to reception. The number of elements 38 in each column is in a range of about 200 to about 600 elements and spans a vertical distance of about 2 to 2.5 meters along axis R; however, in other embodiments, a different vertical span and/or number of elements can be utilized. Transceiver 42 can control switching tree 43 to irradiate body B with only one element 38 of the transmitting column at a time and simultaneously receive with one or more elements 38 of the receiving column. Transceiver 42 includes logic to direct successive activation of each element 38 of the transmitting column and the corresponding one or more elements 38 of the receiving column to provide a scan of a portion of person 22 along a vertical direction with array 36. The corresponding "down range" or "time-of-flight" information can be used to provide positional data about a corresponding portion of person 22 under interrogation. Further information about such arrangements is provided in commonly owned U.S. Pat. No. 5,859,609, which is hereby incorporated by reference.

In a preferred embodiment, transceiver 42 and elements 38 of array 36 are of a form suitable to transmit and/or receive electromagnetic radiation selected from the range of about one Gigahertz to about one Terahertz (about 1 GHz to about 1 THz), which corresponds to a free space electromagnetic radiation wavelength range of about 0.3 meter (m) to about 300 micrometers ($\mu$m). In another preferred embodiment, an impulse transceiver arrangement is utilized that generates frequencies in a range of about 200 MHz to about 15 GHz depending on the impulse width, which corresponds to a free space electromagnetic radiation wavelength range of about 1.5 m to about 0.02 m. In a more preferred embodiment, the frequency range is about 1 GHz to about 300 GHz with a corresponding free space wavelength range of about 0.3 meter to about 1 millimeter (mm). In a most preferred embodiment, the frequency range is about 5 GHz to about 110 GHz with a corresponding free space wavelength range of about 0.06 m to about 2.7 mm.

The transmission pathway for a given element 38 of the transmitting column can be selected to be about the same length as the transmission pathway for the corresponding element(s) 38 of the receiving column to simplify calibration. Nonetheless, in other embodiments, the transmission/reception arrangement can differ. For example, in one alternative embodiment, one or more elements 38 are used for both transmission and reception. In another alternative embodiment, a mixture of both approaches is utilized. Typically, the signals received from array 36 are downshifted in frequency and converted into a processible format through the application of standard techniques. In one form, transceiver 42 is of a bi-static heterodyne Frequency Modulated Continuous Wave (FM/CW) type like that described in U.S. Pat. No. 5,859,609 (incorporated by reference herein). Commonly owned U.S. Pat. Nos. 5,557,283 and 5,455,590, each of which are incorporated by reference herein, provide several nonlimiting examples of other transceiver arrangements. In still other embodiments, a mixture of different transceiver/sensing element configurations with overlapping or nonoverlapping frequency ranges can be utilized that may include one or more of the impulse type, monostatic homodyne type, bi-static heterodyne type, and/or such other type as would occur to those skilled in the art.

Transceiver 42 provides the data corresponding to the array signals to one or more processors 44 of subsystem 40. Processor(s) 44 can each be comprised of one or more components of any type suitable to process the data received from transceiver 42, including digital circuitry, analog circuitry, or a combination of both. Processor(s) 44 can be of a programmable type; a dedicated, hardwired state machine; or a combination of these. For a multiple processor form; distributed, pipelined, and/or parallel processing can be utilized as appropriate. In one arrangement, an integrated circuit form of a programmable digital signal processor is utilized that is capable of at least 1 Gigaflop operation.

Memory 46 is included with processor(s) 44. Memory 46 can be of a solid-state variety, electromagnetic variety, optical variety, or a combination of these forms. Furthermore, memory 46 and can be volatile, nonvolatile, or a mixture of these types. Memory 46 can be at least partially integrated with processor(s) 44. Removable processor-readable Memory Device (R.M.D.) 48 is also included with processor(s) 44. R.M.D. 48 can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, R.M.D. 48 is absent.

Subsystem 40 is coupled to motor 34 to selectively control the rotation of platform 32 with processor(s) 44 and/or transceiver 42. Subsystem 40 is housed in a monitoring/control station 50 that also includes one or more operator input devices 52 and one or more display devices 54. Operator input device(s) 50 can include a keyboard, mouse or other pointing device, a voice recognition input subsystem, and/or a different arrangement as would occur to those skilled in the art. Operator display device(s) 52 can be of a Cathode Ray Tube (CRT) type, Liquid Crystal Display (LCD) type, plasma type, Organic Light Emitting Diode (OLED) type, or such different type as would occur to those skilled in the art. Station 50 is arranged to be controlled by one ore more security point operators responsible for the operation of system 20 as further described hereinafter.

System 20 further includes communication subsystem 60 coupled to subsystem 40 by communication link 62. Subsystem 60 includes network server 63 coupled to computer network 70. Computer network 70 can be provided in the form of a Local Area Network (LAN), a Municipal Area Network (MAN), and/or a Wide Area Network (WAN) of either a private type or publicly accessible type, such as the internet. Link 62 can be provided by such a network or be of a dedicated communication channel variety. Server 63 can be remotely located relative to subsystem 40. Indeed, in one embodiment, server 63 is coupled to a number of remotely located subsystems 40 with corresponding portals 30. In still other embodiments, more than one server 63 can be coupled to a common portal 30 and subsystem 40 arrangement. Alternatively or additionally, server 63 can be an integral part of subsystem 40. For yet other embodiments, server 63, network 70, and sites 80 are absent. Indeed, removable memory device 48 can be used to alternatively or additionally transfer data between subsystem 40 and other computing/processing devices.

Server 63 is operable to communicate over network 70. Computer network 70 communicatively couples a number of sites 80 together. Each site 80 includes computer 82 arranged to communicatively interface with computer network 70. Each computer 82 includes one or more operator input device(s) 50 and one or more operator output device(s) 52 as previously described for subsystem 40, that are not shown to preserve clarity. Device(s) 50 and 52 at each site 80 selectively provide an operator input and output (I/O) capability. Computer 82 can be in the form of another subsystem 40, a personal computer or computer workstation, another computer server, Personal Digital Assistant (PDA), and/or a different configuration as would occur to those skilled in the art. While only two sites 80 are illustrated to preserve clarity, it should be understood that more or fewer can be coupled via computer network 70.

Collectively, server 63, computer network 70, and sites 80 provide an arrangement to remotely communicate with station 50. The interconnection of these components can be hardwired, wireless, or a combination of both. In lieu of or in addition to network 70, one or more of sites 80 and server 63 could be coupled by dedicated cabling or the like. Communication over network 70 can be used to monitor performance of station 50, update software associated with subsystem 40, remotely operate station 50 or portal 30, and/or share data pertinent to the recognition of suspicious objects with system 20 as will be more fully described hereinafter. In one such arrangement, one or more of sites 80 are configured as a repository for data pertinent to security screening with system 20.

Figure 3:
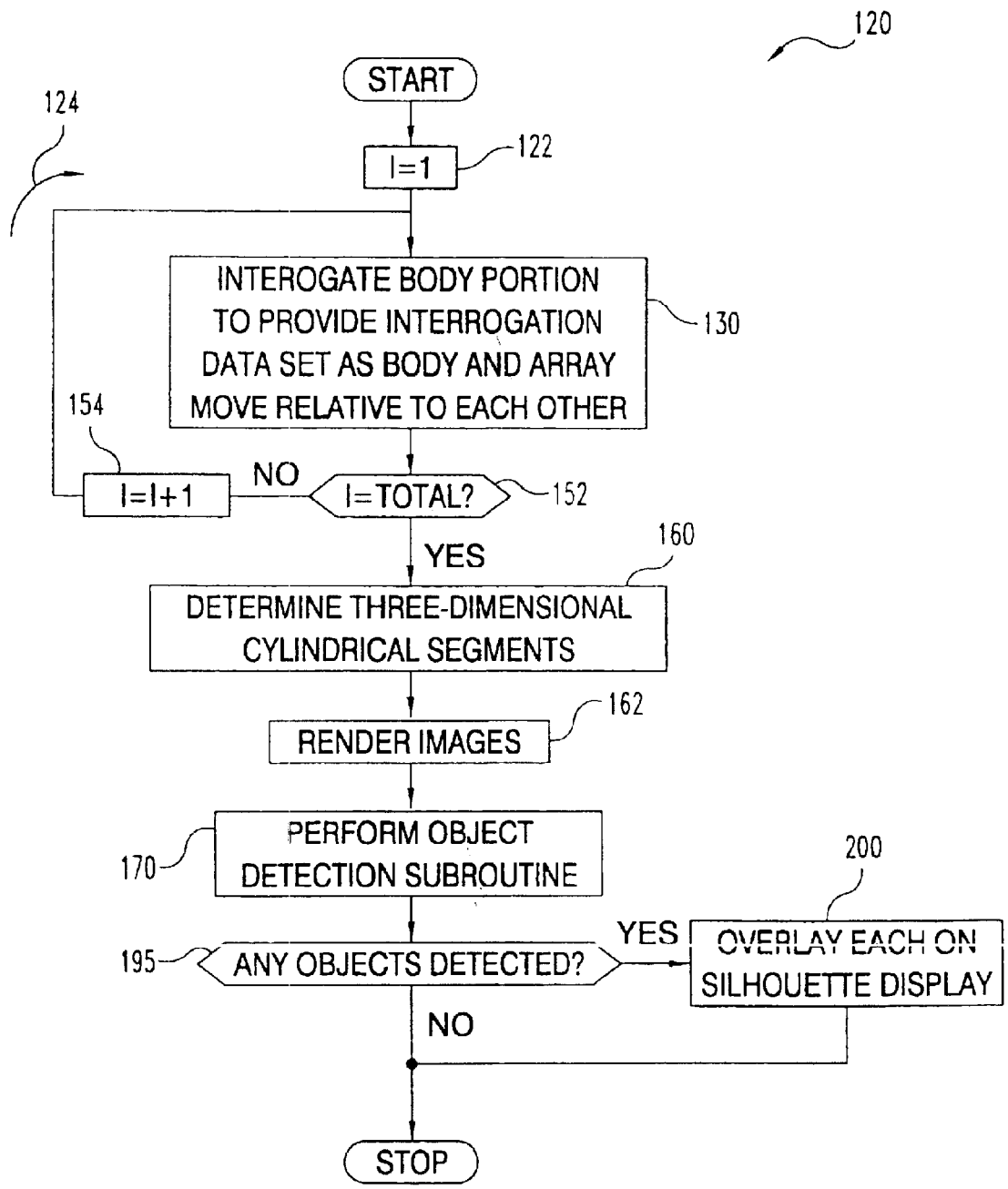
FIGS. 3–5 are flow charts illustrating one procedure for operating the system of FIG. 1.

Referring additionally to the flowchart FIG. 3, one mode of operating system 20 is illustrated as procedure 120. Procedure 120 is performed with system 20 to provide image information representative of person 22 carrying object 25. Procedure 120 begins with operation 121. In operation 121, person 22 enters portal 30 at a security checkpoint to be screened for weapons, contraband, and/or other items/materials. Procedure 120 proceeds to initialization operation 122 that sets interrogation index "I" to one (I=1). From operation 122, procedure 120 enters interrogation loop 124 beginning with interrogation subroutine 130. Interrogation subroutine 130 interrogates a portion of person 22 within a field of view of array 36 as person 22 rotates on platform 32. Index I is an integer index to the number of different interrogation subroutines 130 performed as part of procedure 120.

Figure 4:
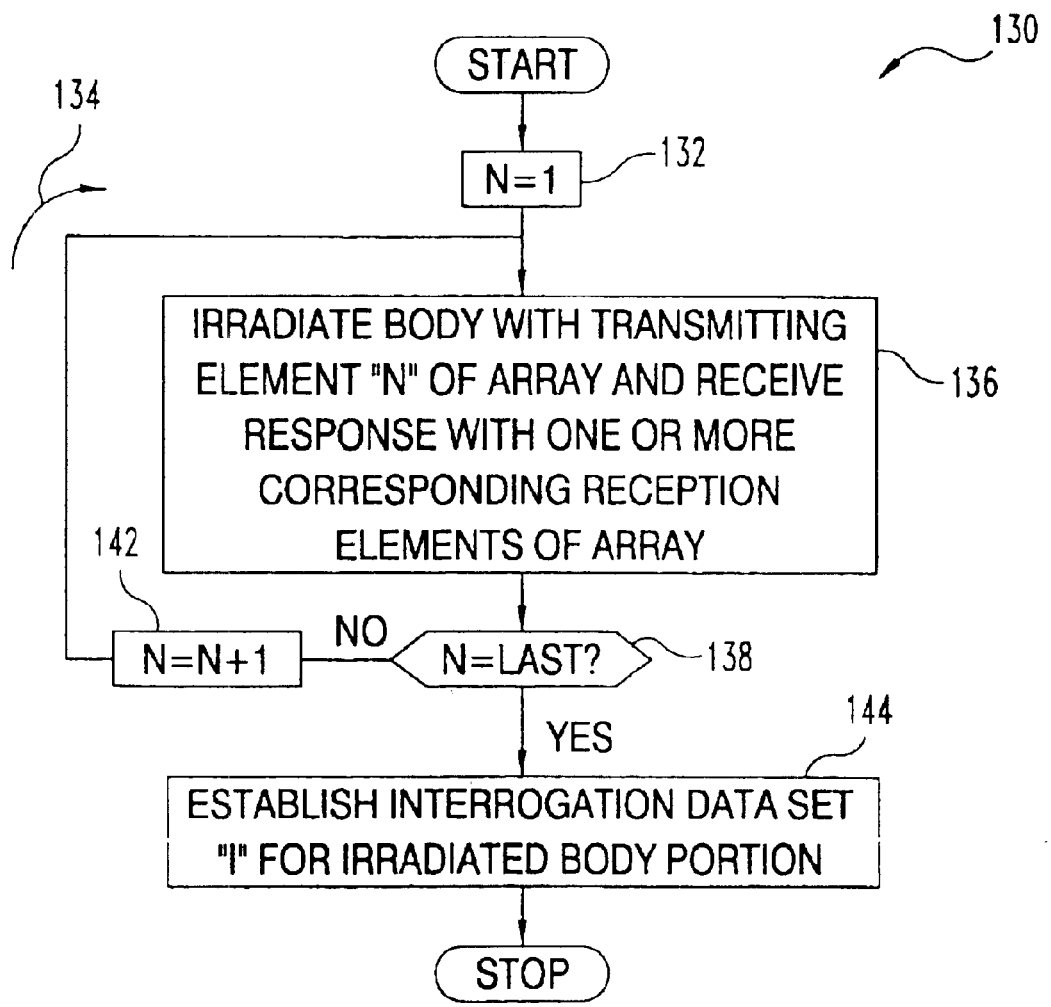

Referring to FIG. 4, interrogation subroutine 130 is further illustrated. Subroutine 130 begins with initialization operation 132 in which transmission index N is set to one (N=1). From operation 132, element sequencing loop 134 is entered, beginning with transmission/reception operation 136. Index N is an integer index to the number of transmission/reception operations 136 performed during subroutine 130. In operation 136, a portion of person 22 in the field of view of a transmitting element number "N" of array 36 is irradiated with electromagnetic radiation and one or more corresponding reception elements collect the reflected electromagnetic radiation in response to the transmission. The transmitting and reception elements are selected by logic of transceiver 42 with switching tree 43 as previously described. From operation 136, subroutine 130 proceeds to conditional 138, which tests whether transmitting element number "N" is the last element needed to transmit (N=LAST?); where LAST is the total number of the transmitting elements to be activated by transceiver 42.

In one form, for each execution of subroutine 130, transmitting element "N" sweeps through a selected frequency range twice, and the corresponding backscatter information for each of the two sweeps is received with a different reception element. The transmitting elements can be staggered relative to the reception elements such that transmitting element N aligns with a point between the two reception elements along a common axis of the array. U.S. Pat. No. 5,557,283 (incorporated by reference) describes an example of this arrangement of transmitting and reception elements. In other forms, a different technique can be utilized involving more or fewer sweeps, different types of sweeps, and/or different transmitting/reception orientations and numbers.

If the test of conditional 138 is negative (N<LAST), then increment operation 142 is performed, incrementing N by one (N=N+1). Loop 134 returns from operation 142 to transmission/reception operation 136 for execution with the transmitting/receiving subset of elements 38 corresponding to the new, incremented value of N from operation 142. In this manner, elements 38 are activated in a vertical path along array 36 with transceiver 42 to provide data along a contiguous region of person 22.

The resolution of interrogation information obtained with transceiver 42 can be enhanced by linearly sweeping through a selected ultrawide frequency range during each operation 136. In one preferred form, transceiver 42 sweeps through a range of at least 10 GHz for each execution of operation 136. This sweep can occur, for example, over a range of about 10 GHz to about 20 GHz. In a more preferred form, transceiver 42 and elements 38 are arranged for a sweep range of 16 GHz. This sweep can occur, for example, over a range of about 24 GHz to about 40 GHz. In one most preferred form, the ultrawide sweep range is selected such that the range resolution is generally the same as the lateral resolution. For these forms, elements 38 are selected to be of a type with a frequency response suitable for the selected sweep range, including, but not limited to the taper slot or end-fire antenna type. In another form, the transmitter can sweep through a given frequency range (such as 10 GHz to 20 GHz) in a pseudo-random order—sometimes known as frequency hopping.

Loop 134 is repeated LAST number of times, sequencing through the desired transmitting/receiving elements 38 of array 36 under the control of transceiver 42. When the test of conditional 138 is true, the affirmative branch proceeds to data operation 144. Data resulting from the execution of operation 136 is provided by transceiver 42 to processor(s) 44. In data operation 144, an interrogation data set is established for the information gathered through the repeated execution of operation 136 from N=1 through N=LAST. This data set corresponds to the current value of integer index I and the portion illuminated during these executions. Initially, the interrogation data set can be accumulated and organized by transceiver 42, processor(s) 44 or both; and then stored in memory 46 for further processing by processor(s) 44 as described in connection with the remainder of procedure 120. From operation 144, subroutine 130 returns to the next stage of procedure 120.

Referring back to FIG. 3, procedure 120 continues with conditional 152 that tests whether the final value of index I has been reached (I=TOTAL?); where TOTAL is the total number of desired executions of loop 124 (and subroutine 130) for procedure 120. If the test of conditional 152 is negative (I<TOTAL), procedure 120 continues to increment operation 154 to increment index I by one (I=I+1). Loop 124 then returns to subroutine 130 for the next execution until I is incremented to be equal to TOTAL.

With the execution of loop 124 TOTAL number of times, TOTAL number of interrogation data sets are stored in memory 46. When the test of conditional 152 is true, procedure 120 continues with cylindrical segmentation operation 160. In operation 160, the interrogation data sets are processed with processor(s) 44 to generate a number of cylindrical image data sets that each correspond to an arc segment of cylinder C. Referring to FIG. 2, arc segment S1 subtends a viewing angle V of about 90 degrees with respect to person 22. Arc segment S1 defines a cylindrical aperture CA that extends along axis R. The image data set corresponding to arc segment S1 represents the three-dimensional surface of body B that is reflective with respect to the selected electromagnetic radiation, as if viewed through cylindrical aperture CA. In one convenient form, the image data set is defined in terms of cylindrical coordinates, although any three-dimensional coordinate system can be used. Each image data set is determined from the interrogation data gathered for the corresponding arc segment by processor(s) 44. Reference is made to commonly owned U.S. Pat. No. 5,859,609 (incorporated herein by reference) for further description about the determination of cylindrical image data.

Figure 6:
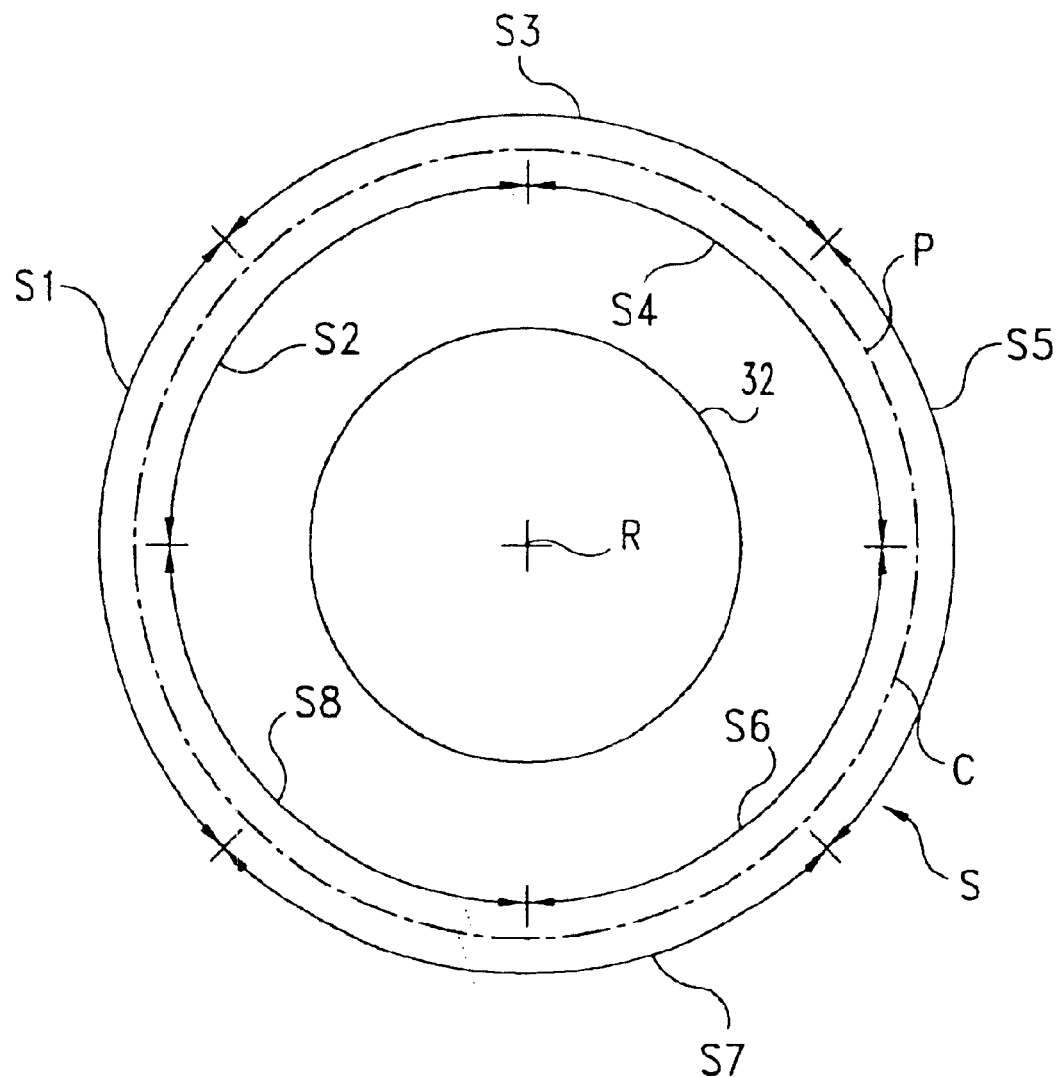
FIG. 6 is a schematic, top view of the system of FIG. 1 illustrating a number of overlapping arc segments.

During operation 160, cylindrical image data sets are determined for a number of arc segments about axis R that collectively circumscribe person 22. In FIG. 6, eight overlapping arc segments S1, S2, S3, S4, S5, S6, S7, and S8 (collectively segments S) are illustrated with respect the generally circular pathway P and corresponding cylinder C. Segments S1, S3, S5, and S7 are schematically represented by double-headed arrows slightly to the outside of path P and segments S2, S4, S6 and S8 are schematically represented by double-headed arrows slightly inside path P to preserve clarity. In FIG. 6, segments S each correspond to a viewing angle of about 90 degrees, and each one overlaps two others by about 45 degrees. It should be understood that each different segment S corresponds to a representation of a different portion of person 22. In other embodiments, the viewing angle can differ and/or may be nonuniform from one arc segment S to the next. Alternatively or additionally, overlap may be intermittent or absent.

Procedure 120 proceeds from operation 160 to operation 162. In operation 162, image data obtained for each segment S is utilized by processor(s) 44 to render corresponding two-dimensional images. These images are provided as two-dimensional arrays of pixel intensities. While the two-dimensional rendering can be displayed using device(s) 54 it is generally not desirable to do so at this stage because of the possibility that private body parts beneath clothing may be revealed. Operation 162 results in a number of adjacent images or frames of person 22 corresponding to the different arc segments S.

Figure 5:
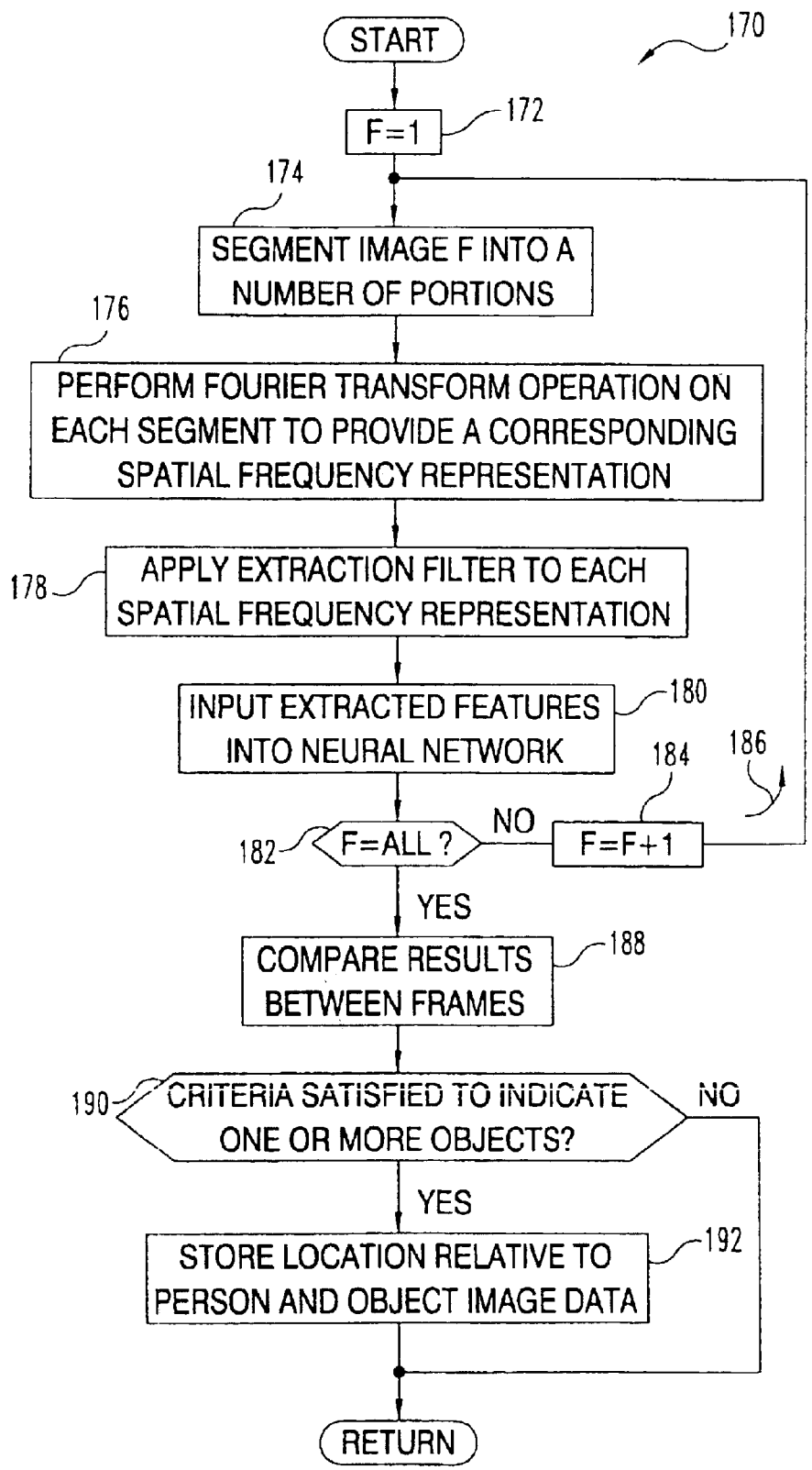

From operation 162, procedure 120 continues with the performance of object detection subroutine 170. In subroutine 170, numerical processing of image data is performed to determine if one or more suspicious objects are being carried by person 22, such as concealed object 25 shown in FIG. 1. Referring to FIG. 5, subroutine 170 is shown in greater detail. Subroutine 170 begins by setting image counter F to 1 (F=1) in operation 172. Counter F indexes the adjacent images from operation 162 for processing in subroutine 170. From operation 172, subroutine 170 proceeds to operation 174. In operation 174, the current image F is segmented or broken-up into a number of portions.

Figure 7:
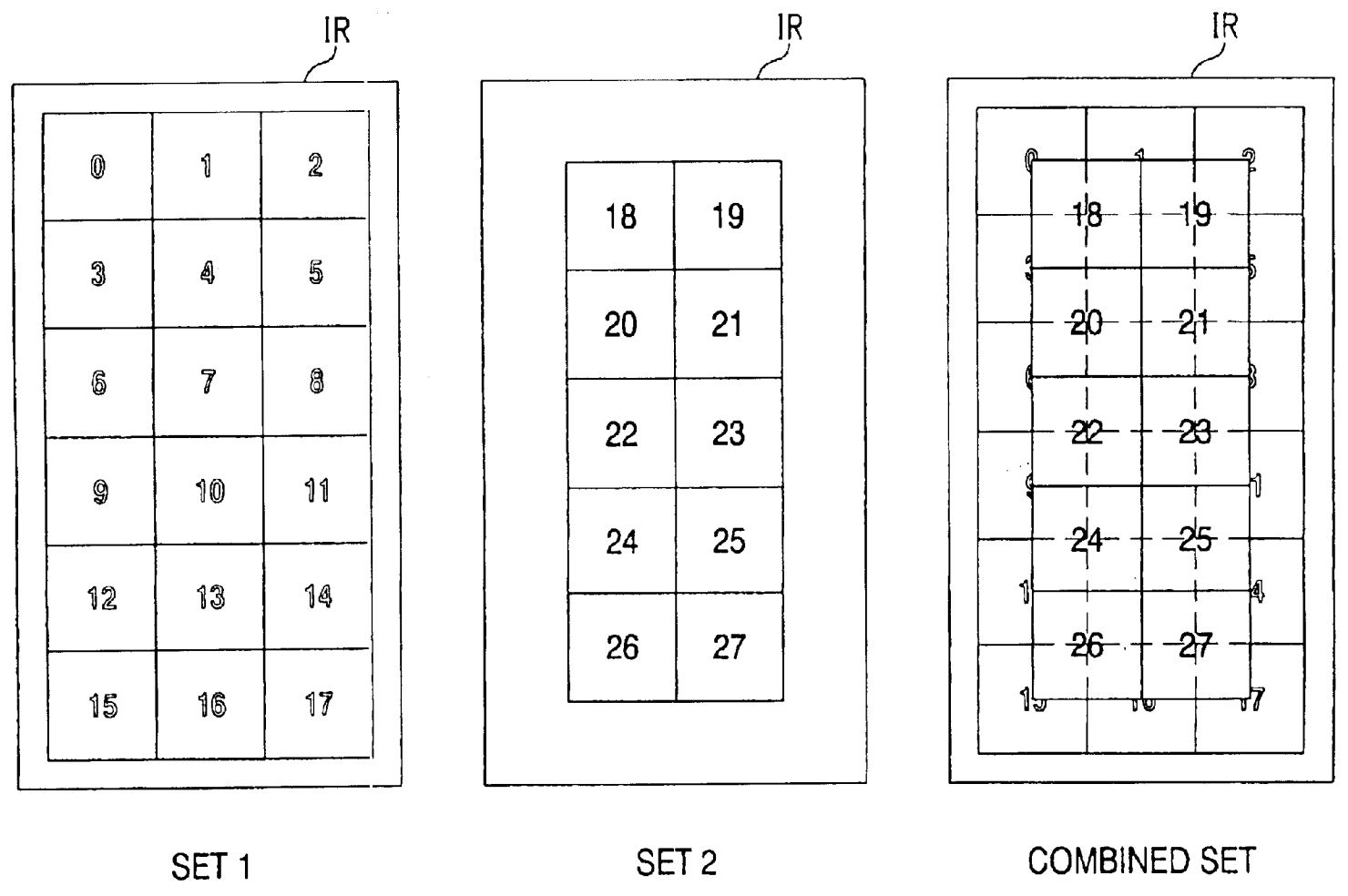

Referring additionally to FIG. 7, a rectangular image region IR is illustrated in three adjacent fields. In the leftmost field, image region IR is segmented into a first set, Set 1, of image portions numbered 0–17. In the middle field, image region IR is segmented into a second set, Set 2, of image portions numbered 18–27. Image portions 0–17 overlap image portions 18–27 as illustrated in the combined set in the rightmost representation of image region IR in FIG. 7. In one embodiment, the size of a segment is selected to be large enough to contain most of the region necessary to indicate a common object type of interest, but not so large as to make it difficult to localize such an object. In one arrangement utilizing Ku-band electromagnetic radiation, a segment size of about 32 by 32 pixels was found to be desirable. Nonetheless, in other embodiments, other sizes, shapes, patterns, degrees of uniformity, and/or different attributes may be varied as would occur to those skilled in the art with or without overlapping portions.

Referring back to FIG. 5, subroutine 170 continues with operation 176. In operation 176 image data for each segment undergoes a Fourier transformation into Fourier spatial frequency space. Operation 176 can be performed with subsystem 40 to provide a corresponding spatial frequency representation for each image segment. Typically, such a representation is complex-valued. It has been found that man-made objects often have a spatial frequency representation that typically has a higher percentage of upper spatial frequencies relative to natural objects, such as the human body. Also, spatial frequency representations for man-made objects tend to dominate in certain directions in a spatial frequency distribution over Fourier space. Such distinctions can be utilized to classify image portions suspected of revealing a man-made object.

Figure 8:
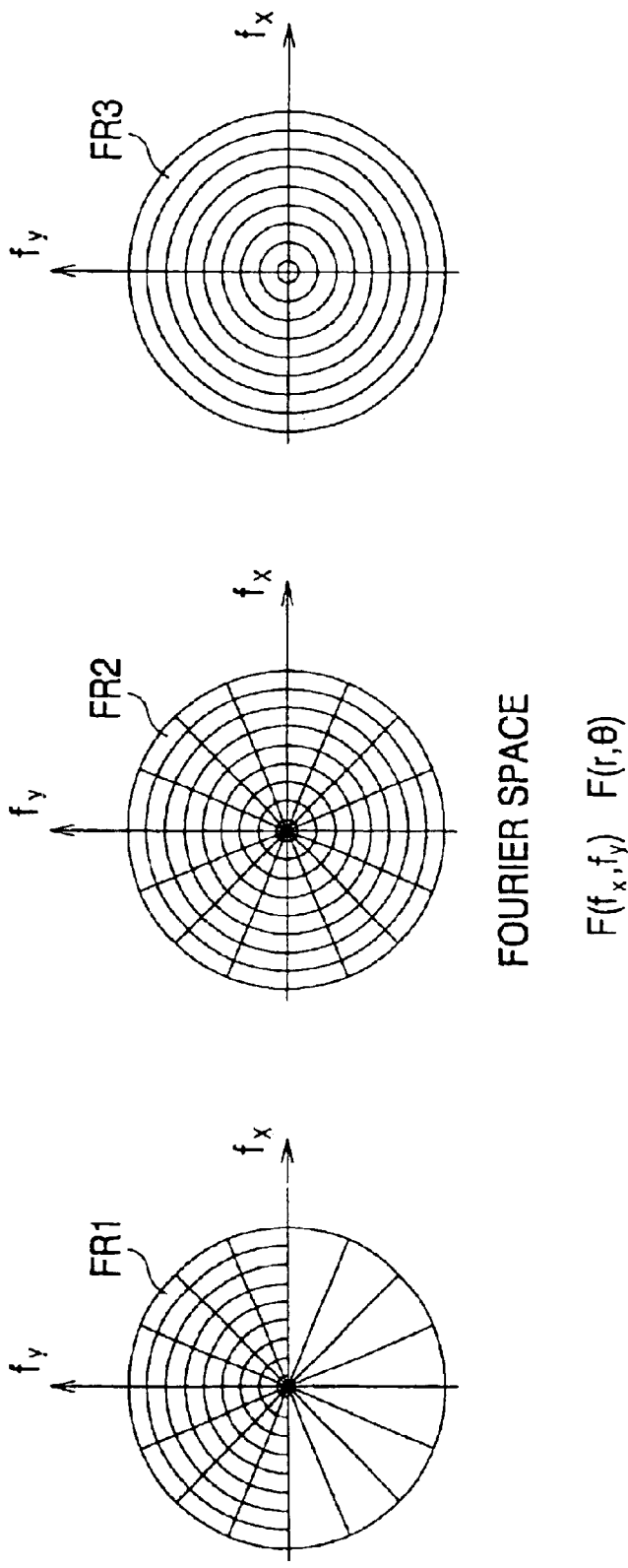
FIG. 8 is a diagram comparing three different types of feature extraction filters for use with the procedure of FIGS. 3–5.

Because spatial frequency information of the type provided by a Fourier transform operation typically involves complex values, it is often desirable to simplify the data as part of the object detection procedure. In operation 178, an extraction filter is applied to extract features from the spatial frequency representation that may be indicative of a man-made object. Referring additionally to FIG. 8, three different feature extractor filters FR1, FR2, and FR3 are illustrated in diagrammatic form relative to Fourier space. Feature extractor FR1 is of a ring-wedge configuration, including a half-plane of wedges and a half-plane of rings centered on the zeroth ($0^{th}$) frequency component in Fourier space. For this extractor, the wedges provide scale invariance and the rings provide rotational invariance. Extraction filter FR2 is of a sector configuration. By integrating spatial frequencies within each sector, a set of features representing angular and radial aspects of the corresponding image segment can be generated. While not invariant, extraction filter FR2 can be utilized to identify objects having preferred orientations and/or sizes. Extraction filter FR3 is of a ring configuration that is rotation invariant and so represents a segment based on a radial spatial frequency component. In operation 178, one or more of these extraction filter types (FR1, FR2, FR3) can be applied and/or a different type of extraction filter may be utilized. In still other embodiments, extraction at this stage may be absent.

In operation 180, features extracted during operation 178 are input into a neural network defined with subsystem 40. In one form, the extracted features are input into a multilayer perceptron form of neural network. The network is configured for object identification through a repetitive training process, such as a back propagation of error algorithm. In still other embodiments, a different type of neural network and/or training technique may be additionally or alternatively utilized. In yet further embodiments, a different type of adaptive processing technique can be utilized in addition to or as an alternative to a neural network, such as fuzzy logic, an operated-assisted expert learning system, or the like. Alternatively or additionally, nonadative processing can be utilized.

From operation 180, subroutine 170 continues with conditional 182 which tests whether all the images have been processed in accordance with operations 174–180. If not, counter F is indexed (F=F+1) in operation 184 and loop 186 returns to operation 174 to process the next image. If conditional 182 is affirmative, subroutine 170 continues with operation 188 in which the results obtained from loop 186 for different image frames are compared to determine if they are consistent with one other. In one nonlimiting example with respect to arc segments S, the image results for arc segments S1 and S2 could be compared to each other to the extent they overlap (see FIG. 6). Likewise overlapping image results for arc segment pairs S2 and S3, S3 and S4, S4 and S5, S5 and S6, S6 and S7, S7 and S8, and S8 and S1 can be compared for consistency during operation 188. In other embodiments, more or fewer frames and/or a different frame-to-frame comparison can be made. In yet other embodiments, there is no frame-to-frame comparison made at all.

From operation 188, conditional 190 is encountered in which frame comparison results and/or one or more other desired detection threshold/criterion are tested to determine if any objects of interest are indicated. If such objects are indicated, then the relative location to the person and object image data is stored in operation 192. If the test of conditional 190 is negative then subroutine 170 returns, bypassing operation 192. It should be understood that the performance of any of operations 174–180 and 188, and/or conditional 190 can involve comparing processing results to one or more threshold valves or other criteria to determine if a corresponding image, image portion or representation, image feature, or the like indicates an object of interest. Any such criteria can be static or dynamic in nature. Dynamic criteria may be operator adjustable, adaptively machine adjusted, and/or selectively changed through a different technique as would occur to those skilled in the art.

Referring back to FIG. 3, once subroutine 170 is completed, procedure 120 continues with conditional 195 which tests whether any objects were detected with subroutine 170. If objects were detected, procedure 120 continues with operation 200. In operation 200, an image of each of the one or more detected objects is displayed with output device(s) 54. The object image or images overlay a silhouette of person 22 to show relative location with a gender-neutral representation. In this way, the displayed image can be adjusted to hide/conceal body features to which a privacy objection might be made if displayed. Alternatively, the rendering can include a schematic body image similar to a mannequin, a wire-frame body, or other gender-neutral representation. In one form, the suspect image features can be highlighted by a contrasting visual characteristic such as color, blinking/flashing or other intensity variation, and the like. Based on such a display, an operator can determine if further inspection is warranted, if person 22 should be detained as a security risk, and the like. Optionally, visual and/or audible alert signals can be generated in operation 200 to focus the operator's attention on the person undergoing inspection and/or the corresponding image and/or information pertaining to the classification and detection of the objects can be displayed in text or graphic form for operator consideration. As another option, different views of the person and/or suspect image regions can be displayed simultaneously. Alternatively or additionally, an operator can switch between different views and/or can zoom-in or zoom-out to change relative size of an image being displayed using input device(s) 52. In still other embodiments, false alarms can be used to refine detection criteria as/if desired.

After execution of operation 200, procedure 120 terminates. Also, if conditional 195 is negative, procedure 120 terminates, bypassing operation 200. Accordingly, an operator only reviews images that are indicated to show one or more objects of interest, such as a weapon or contraband. Accordingly, privacy concerns are at the very least reasonably reduced if not completely eliminated. In still other embodiments, display of images of the body beneath clothing may be conditionally or unconditionally acceptable, or may be altogether absent. Alternatively or additionally, the information gathered with subsystem 40 is sent via computer network 64 to one or more remote sites 80. Sites 80 can perform some or all of the data processing of procedure 120 in lieu of processor(s) 44. In one process, a clothed individual is nonintrusively scanned by portal 30 and the image information is sent via server 63 and network 70 to a designated computer 82. Alternatively or additionally, background information about a person carrying an object of interest can be accessed via server 63 and network 70.

For procedure 120, transceiver 42 and processor(s) 44 include logic to perform the various operations described. This logic can be in the form of software programming instructions, firmware, and/or of a hardwired form, just to name a few. Furthermore such logic can be in the form of one or more signals carried with memory 46, R.M.D. 48, and/or one or more parts of computer network 70. In one example, logic signals to perform one or more operations is transmitted to or from processor(s) 44 via network 70. Alternatively or additionally, programming for processor(s) 44 is transported or disseminated through R.M.D. 48 and/or one or more other storage devices.

Figure 9:
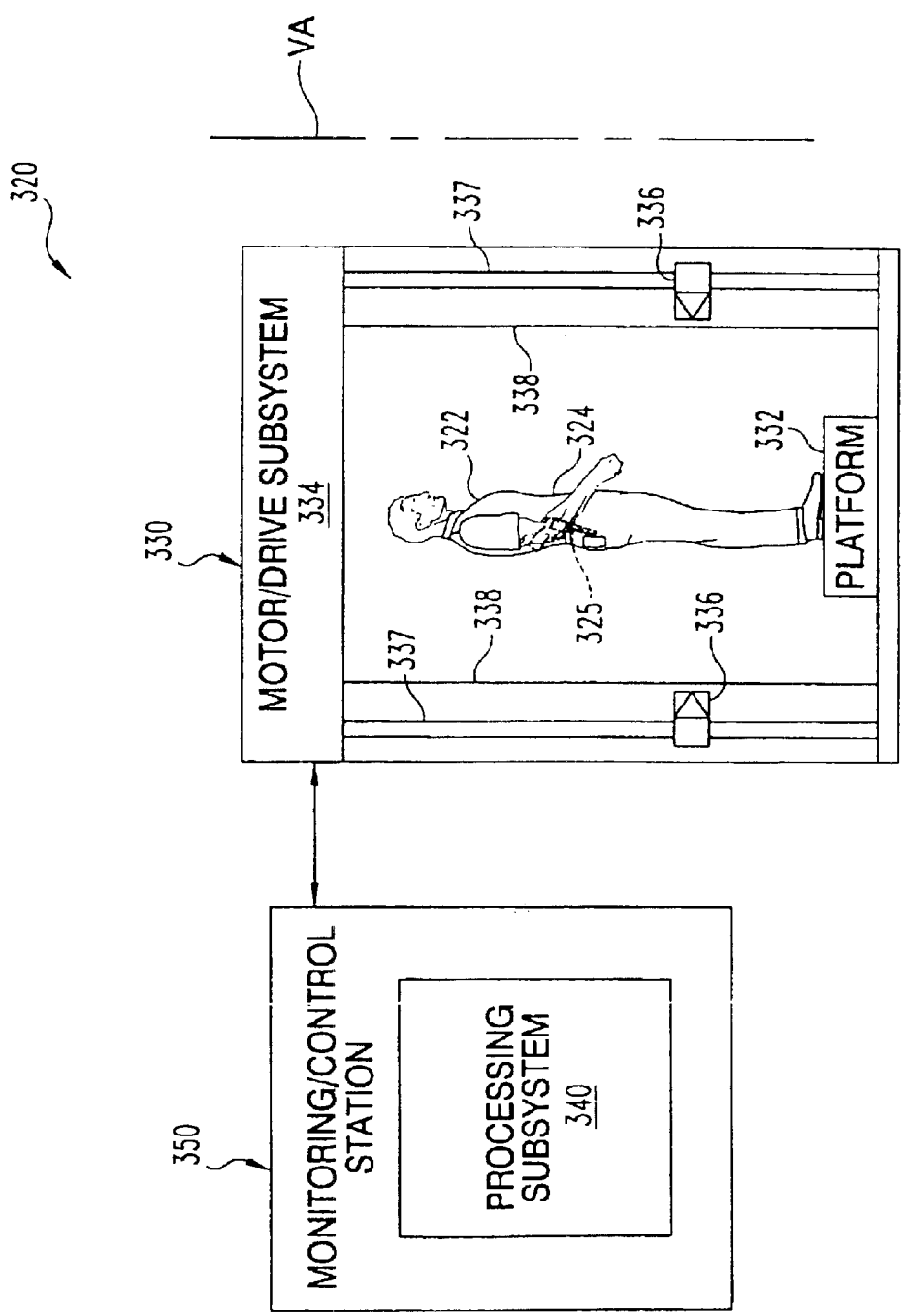
FIG. 9 is a partial, diagrammatic view of another system.
Figure 10:
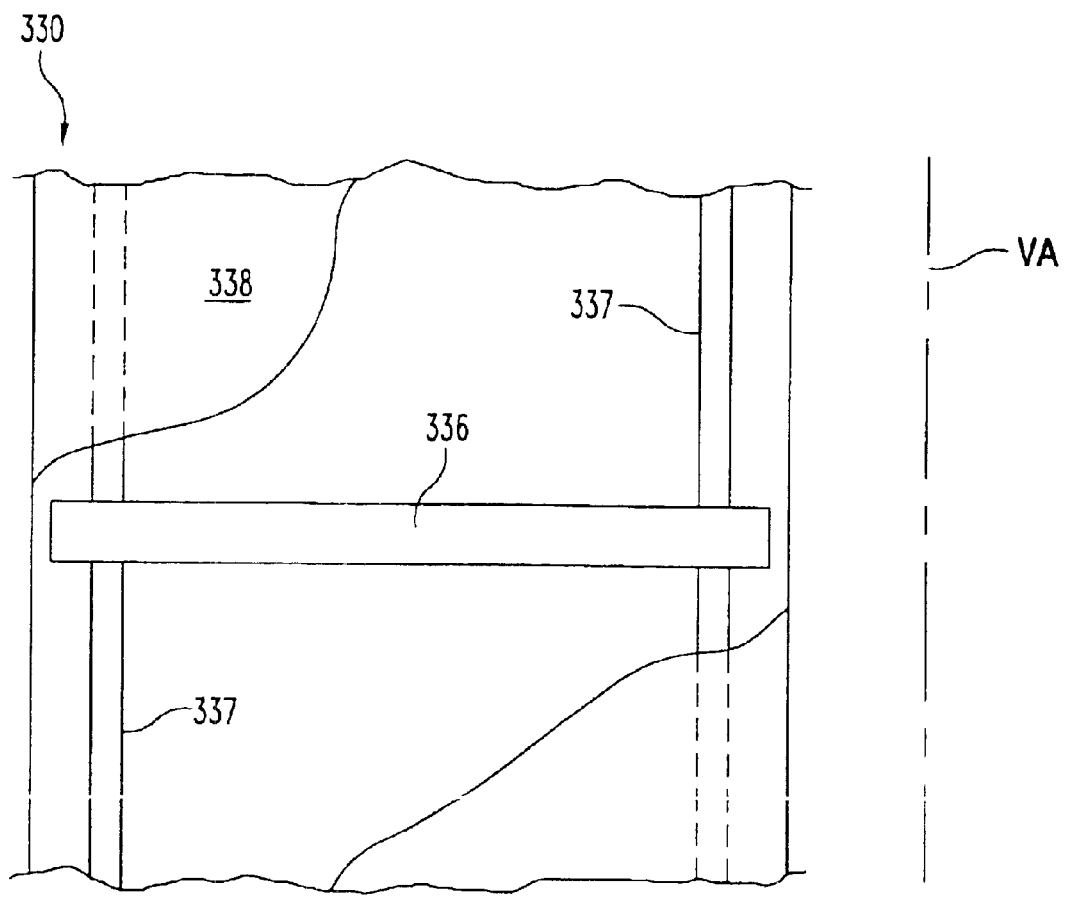
FIG. 10 is a partial, cut-away view of the portal shown in FIG. 9.

FIGS. 9 and 10 illustrate system 320 of another embodiment of the present invention that can be used to perform procedure 120. System 320 illuminates person 322 which selected electromagnetic radiation in the manner described in connection with system 20. For system 320, person 322 is wearing clothing articles that conceal object 325 shown in phantom. As in the previously described embodiment, system 320 can be used to interrogate inanimate objects as well. System 320 includes dual planar panel scanning portal 330 and processing subsystem 340 included in monitoring/control station 350. Portal 330 is coupled to processing subsystem 340 and can be configured the same as subsystem 40, accounting for differences in the scanning technique of portal 330 as is more fully described hereinafter. Station 350 includes one or more operator input and output devices as described in connection with system 20 that are coupled to subsystem 340. Station 350 can be arranged to provide a security checkpoint operator interface adjacent portal 330.

Portal 330 includes stationary platform 332 arranged to support person 322 and overhead motor/drive subsystem 334. Under the control of subsystem 340, subsystem 334 is configured to controllably slide each of two arrays 336 along corresponding guide rods 337 up and down with respect to vertical axis VA. Correspondingly, arrays 336 each follow a generally linear path on opposite sides of person 322 and are each included within a corresponding opposing panel 338. FIG. 10 shows one of panels 338 in greater detail utilizing a partial cut-away view. In system 320, subsystem 340 is configured the same as subsystem 40 of system 20, is likewise arranged to perform procedure 120, and can include a transceiver and/or switching tree as appropriate. However, during performance of procedure 120, the operation of subsystem 340 accounts for the movement of array 336 relative to person 322 in a linear, translational manner instead of a rotational manner as described in connection with system 20. Also, because the opposing arrays 336 do not provide overlapping frames as in the case of system 20, operation 188 of subroutine 170 is not performed and appropriate adjustments are otherwise made to procedure 120. System 320 can include one or more encoders (not shown) operably coupled to system 340 and/or other devices/techniques to track position of arrays 336 relative to platform 332. System 320 can further include a communication subsystem (not shown) the same as subsystem 60 to remotely communicate with subsystem 340.

In one particular arrangement, panels 338 are spaced apart by about 1.22 meters and a frequency sweep in the Ku-band from about 12.5–18 GHz is performed to provide a lateral resolution of about 1 centimeter and a depth resolution of about 2.7 centimeters. For this arrangement, arrays 336 each include two subarrays of about 56 elements each that are arranged back-to-back. One subarray is dedicated to transmission and the other subarray is dedicated to reception within each array 336. In one form, each subarray is fabricated with slot-line antennas spaced apart from one another by about 2 centimeters. During operation, each subarray is electronically scanned from element to element as the scanner moves rapidly over the vertical length of person 322. As the array moves, a number of scans are performed with array 336. During each scan, only one element of the transmitting subarray is illuminating the person and only one element of the receiving subarray is collecting reflected electromagnetic radiation at any given time. Accordingly, each transmitting element and each receiving element is activated in accordance with a desired sequence during the scan. In a FM/CW heterodyne transceiver configuration of this arrangement, the 5.5. GHz frequency sweep is performed in about 12.75 microseconds. In still other embodiments, a different number, size, or type of linear array arrangement can be utilized as would occur to those skilled in the art. In still other examples, different types of rotating and/or linear scanning arrays can be utilized separately or in combination.

Figure 11:
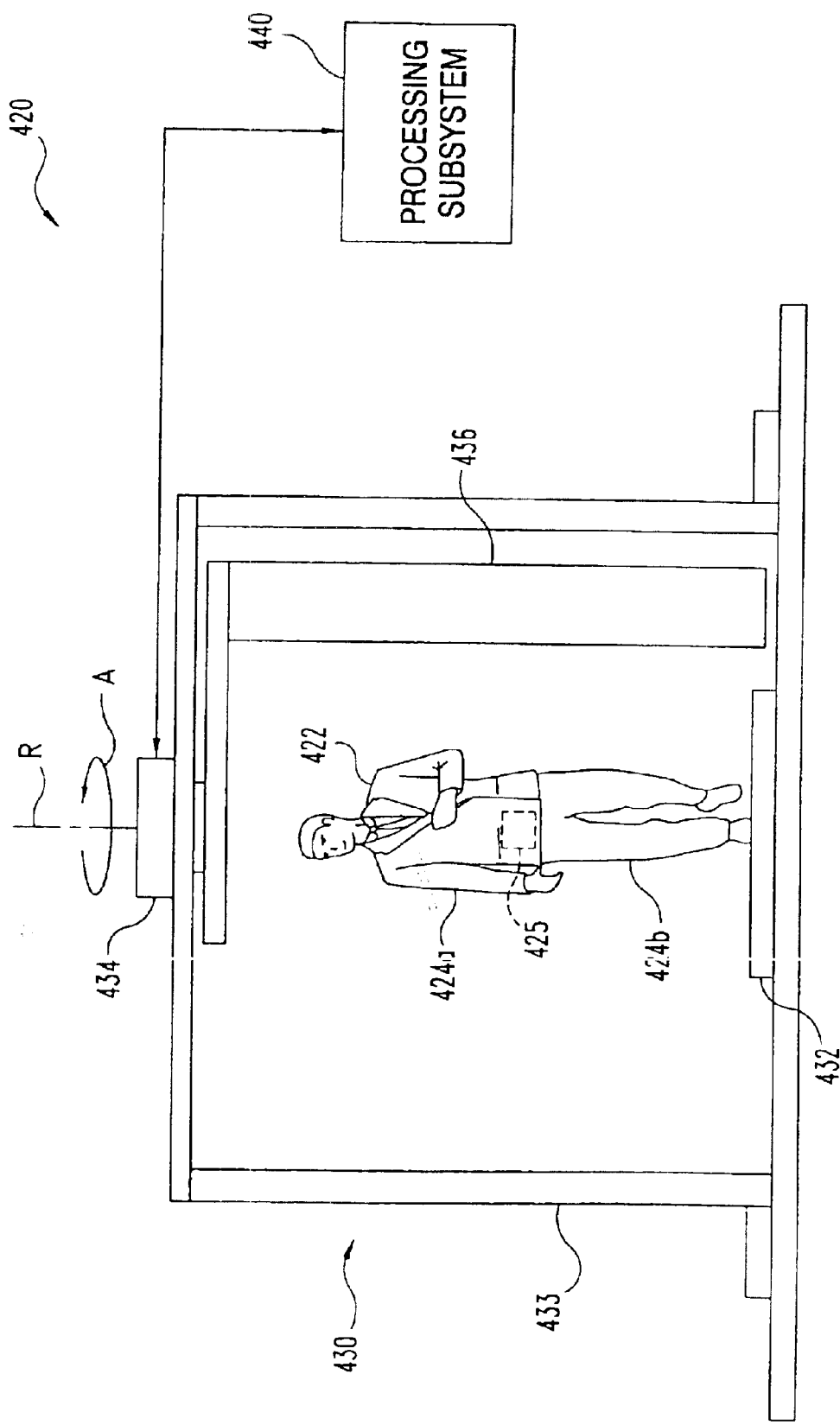
FIG. 11 is a partial, diagrammatic view of still another system.

FIG. 11 illustrates interrogation system 420 of another embodiment of the present invention. System 420 illuminates person 422 with selected electromagnetic radiation in the manner described in connection with system 20. For system 420, person 422 is wearing clothing articles 424a and 424b that hide object 425. As in previously described embodiments, system 420 can be used to interrogate inanimate objects as well.

System 420 includes scanning booth 430 coupled to control and processing subsystem 440. Scanning booth 430 includes stationary platform 432 arranged to support person 422 and frame 433 to support motor 434 coupled to array 436. In contrast to the platform rotation of portal 30 and translational movement associated with portal 330, scanning booth 430 selectively rotates array 436 about rotational axis R and platform 432 during interrogation. For this arrangement, array 436 follows a generally circular pathway to provide a corresponding imaginary cylinder about platform 432. In one form suitable for scanning a person in the standing position, the radius of this cylinder is about 1 meter. Array 436 is otherwise configured the same as array 36.

In system 420, subsystem 440 is configured the same as subsystem 40 of system 20 and is likewise arranged to perform procedure 120 to detect concealed/hidden objects. However, during the performance of procedure 120, the operation of subsystem 440 accounts for the movement of array 436 relative to platform 432 instead of the movement of platform 32 relative to array 36 as for system 20. System 420 can include one or more encoders (not shown) operatively coupled to subsystem 440 and/or other devices/techniques to track the position of array 436 relative to platform 432. System 420 can further include a communication subsystem (not shown) the same as subsystem 60 to remotely communicate with subsystem 440.

Figure 12:
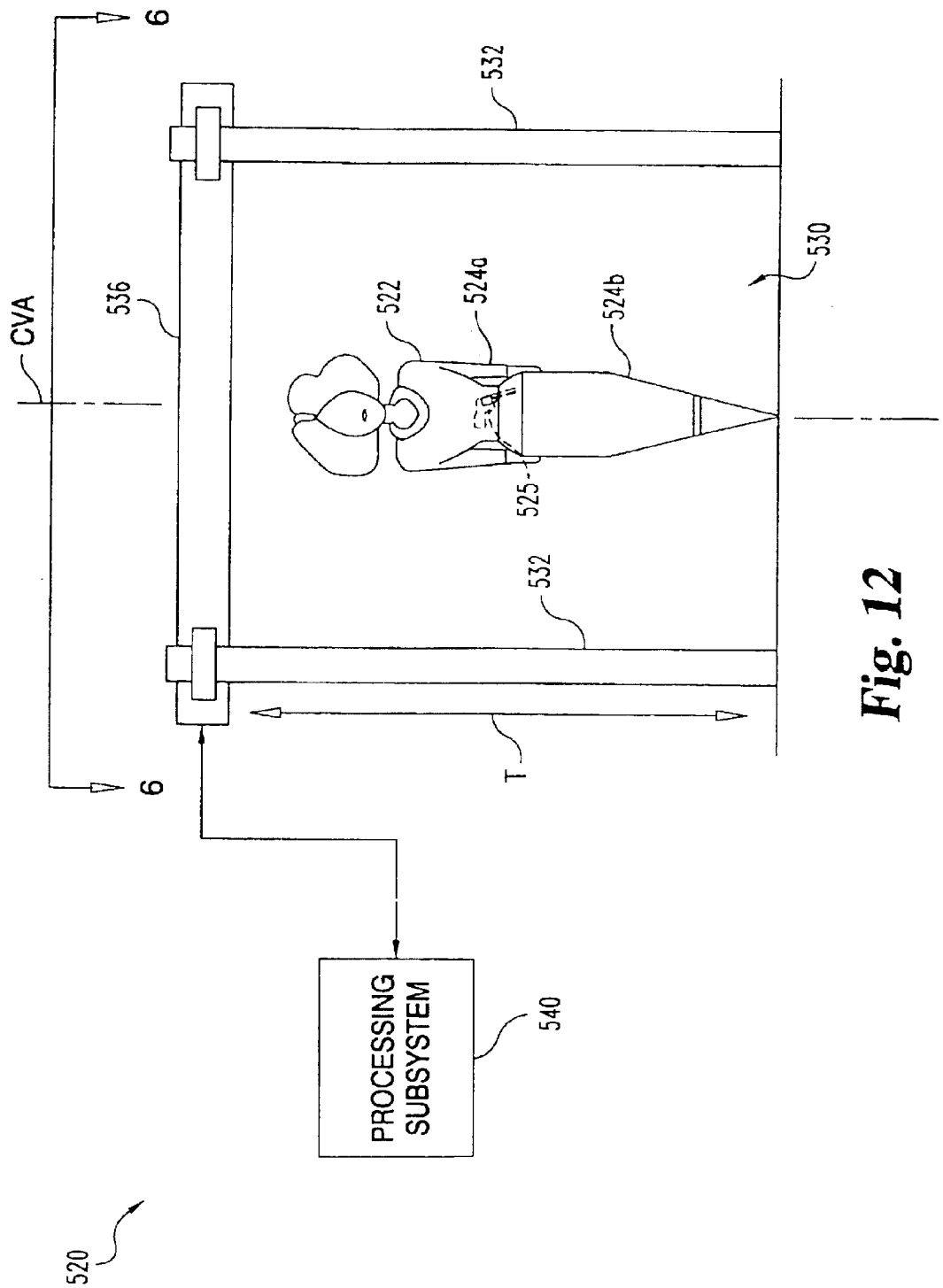
FIG. 12 is a partial, diagrammatic view of yet another system.

FIG. 12 illustrates electromagnetic radiation interrogation system 520 of yet another embodiment of the present invention. System 520 illuminates person 522 with selected electromagnetic radiation of the type previously described. For system 520, person 522 is wearing garments/clothing designated by reference numerals 524a and 524b that conceal object 525. As in previously described embodiments, system 520 can be used to interrogate animate or inanimate objects.

System 520 includes scanning booth 530 coupled to control and processing subsystem 540. Scanning booth 530 includes frame 533 arranged to receive person 522 and support array 536. In contrast to the linearly oriented arrays 36, 336, and 436 of previously described systems 20 and 420, array 536 is arranged as a ring or hoop generally centered with respect to centerline vertical axis CVA. A number of electromagnetic radiation transmitting/receiving elements are arranged in a generally circular pathway along the ring. These elements operate to interrogate person 522 with electromagnetic radiation including one or more wavelengths in the millimeter, microwave, and/or adjacent wavelength bands. Array 536 is arranged for translational movement along axis CVA to scan person 522 as represented by arrow T. One or more motors or other prime mover(s) (not shown) are utilized to selectively move array 536 along axis CVA.

Figure 13:
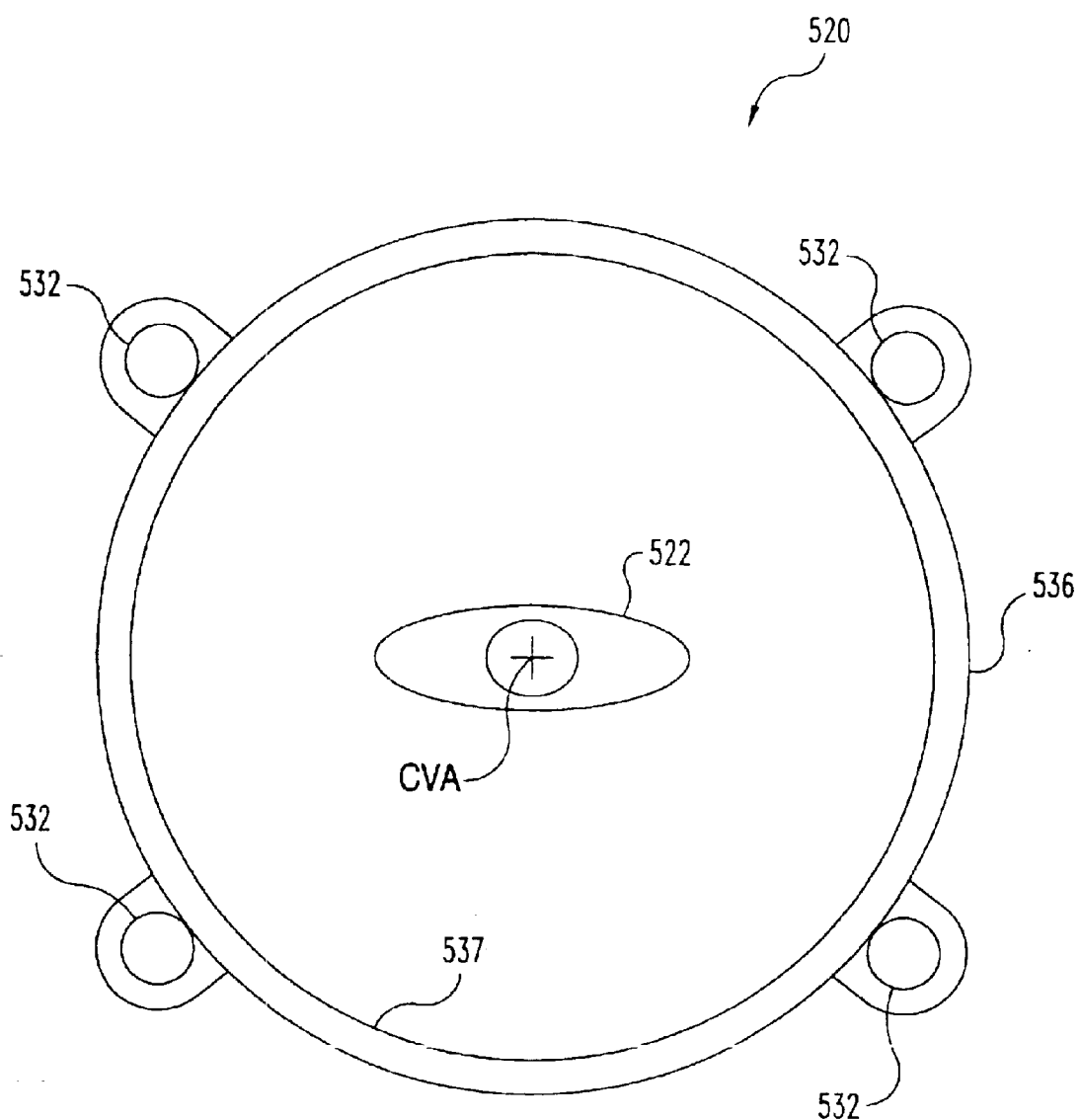
FIG. 13 is a partial, top view of the system of FIG. 12.

Referring further to the partial top view of FIG. 13, array 536 is sized with opening 537 to receive person 522 therethrough as array 536 moves up and down along axis CVA. In FIG. 13, axis CVA is generally perpendicular to the view plane and is represented by crosshairs. With the vertical motion of array 536, an imaginary cylinder is defined about person 522 in accordance with the circular path defined by the array ring; however, neither person 522 nor array 536 is rotated relative to the other, instead translational movement of array 536 is used to scan person 522 vertically.

Subsystem 540 is configured the same as subsystems 40, 340 and 440 and is operable to perform procedure 120, except that processing of subsystem 540 is adapted to account for the vertical translational movement of array 436 with its circumferential arrangement. System 520 can further include a communication subsystem (not shown) the same as subsystem 60 to remotely communicate with subsystem 440. Like previously described embodiments, system 520 is used to detect concealed objects as explained in connect with procedure 120.

Compared to array 36, a larger number of transmitting/receiving elements is typically needed for array 536 to have a comparable resolution to previously described embodiments. In one comparison, between 500 and 2000 transmitting/receiving elements would be desired for array 536 versus 200 to 600 for array 36 for comparable resolution, depending on the frequency band selected. However, under appropriate conditions, scanning booth 530 can perform a scan substantially faster than portal 30. In one nonlimiting example, the scan time for portal 30 is in a range of about 10 to 20 seconds versus about 2 to 5 seconds for scanning booth 530.

In a further embodiment of the present invention, the body undergoing interrogation and the array both move. In one such example, array elements are arranged in an arc segment that can move vertically while the body rotates. In another example, both the array and body rotate. The processing of interrogation data can be adjusted for these different motion patterns using techniques known to those skilled in the art.

In another embodiment, the interrogation and corresponding image information do not correspond to the full circumference of the body undergoing interrogation. Instead, the segment of interest can be less than 360 degrees. For such embodiments, the image information can still be determined by combining data corresponding to two or more different view angles. Alternatively or additionally, less than the full height, width, and/or length of the subject may be scanned in other embodiments. For such alternatives, the array size and/or scanning pattern can be correspondingly adjusted.

In one further embodiment, the image information is obtained in accordance with procedure 120 and/or system 20, 320, 420, or 520 is additionally utilized to identify an individual. One form of this embodiment includes a technique to control access to a restricted area, comprising: scanning an individual attempting to gain access to the restricted area; determining whether the individual is concealing any objects from the scan; comparing one or more aspects of the corresponding image information regarding features of the individual to data stored for those permitted access to the restricted area; and allowing access to the restricted area by the individual if there is a favorable comparison and no suspicious concealed objects are indicated. The determination of a match can be used to activate a gate or other access control device. In another embodiment, image information gathered with system 20, 320, 420, and/or 520 is additionally or alternatively used to identify individuals for which access should not be permitted, such as suspected criminals, known terrorists, and the like. In one more variation of such embodiments, one or more other biometrics (such as a fingerprint, palm print, retina image, vocal pattern, etc.) of the individual are compared in addition to the topographical representation related data as part of the determination of whether to allow access. The features used for identification can be changed for each access to reduce the likelihood that the access control measures will be circumvented. Alternatively or additionally, object detection in accordance with the present invention can be used to determine if an individual is taking an object from an area without permission to do so. Any of these embodiments can be provided as a method, apparatus, system, and/or device.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method, comprising:
   irradiating a person at least partially covered with clothing;
   detecting electromagnetic radiation within a frequency range of about 200 MHz to about 1 THz reflected from a surface beneath the clothing in response to said irradiating;
   establishing data representative of an image of the person from the electromagnetic radiation;
   determining a number of data sets from the data, the data sets each corresponding to a spatial frequency representation of a different portion of the image; and
   adaptively processing each of the data sets to identify a man-made object being carried by the person beneath the clothing.

2. The method of claim 1, wherein said determining includes performing a Fourier transform operation for each of a number of different portions of the data to provide a corresponding number of complex spatial frequency data representations.

3. The method of claim 2, wherein said determining further includes applying an image feature extraction filter to each of the complex spatial frequency data representations to correspondingly provide the data sets.

4. The method of claim 3, wherein said extracting is performed with at least one of a radially invariant and an angular invariant filter.

5. The method of claim 1, wherein said adaptively processing is performed with a neural network.

6. The method of claim 1, wherein the man-made object is at least one of a weapon and contraband.

7. The method of claim 1, which includes displaying an image of at least a portion of the man-made object.

8. A method, comprising:
   establishing data corresponding to an image of a concealed surface by irradiating with electromagnetic radiation including one or more frequencies in a range of about 200 MHz to about 1 THz;
   generating a data set corresponding to a spatial frequency representation of at least a portion of the image from the data; and
   identifying a concealed man-made object by analyzing the data set with a neural network.

9. The method of claim 8, which includes displaying an image of at least a portion of the man-made object.

10. The method of claim 8, wherein said establishing is performed by scanning a person in a portal at a security checkpoint with the electromagnetic radiation.

11. The method of claim 8, wherein said generating includes performing a Fourier transform operation and extracting the data set from results of the Fourier transform operation.

12. The method of claim 8, wherein the range is about 5 GHz to about 110 GHz.

13. The method of claim 8, wherein the concealed man-made object is being carried by a person beneath clothing during said establishing and the man-made object is at least one of a weapon and contraband.

14. The method of claim 8, which includes generating a number of overlapping image frames and wherein said identifying further includes comparing information between two or more of the frames.

15. A method, comprising:
   irradiating a person at least partially covered with clothing;
   detecting electromagnetic radiation reflected from a surface beneath the clothing in response to said irradiating;
   establishing data corresponding to a spatial frequency representation of the surface from the electromagnetic radiation; and
   analyzing the data with a neural network to identify a man-made object being carried by the person beneath the clothing.

16. The method of claim 15, which includes determining a data set corresponding to an image of the surface from the electromagnetic radiation.

17. The method of claim 16, wherein said establishing includes:
   determining a number of image portions from the data set;
   performing a Fourier transform operation for each of the image portions to provide a corresponding number of spatial frequency image portion representations; and
   applying a feature extraction filter to each of the spatial frequency image portion representations.

18. The method of claim 17, wherein the data corresponds to the output of the feature extraction filter for one or more of the spatial frequency image portion representations.

19. The method of claim 15, which includes displaying an image including the man-made object.

20. The method of claim 15, wherein the electromagnetic radiation includes one or more frequencies is a range of about 200 MHz through about 1 THz and the man-made object is at least one of a weapon and contraband.

21. A method, comprising:

irradiating a person at least partially covered by clothing with electromagnetic radiation including one or more frequencies in a range of 200 MHz to about 1 THz;

in response to said irradiating, establishing data representative of an image corresponding to appearance of one or more private body parts under the clothing;

determining a number of data sets each corresponding to a respective one of a number of different image portions;

numerically processing the data sets relative to one or more criteria to evaluate if one or more of the different image portions reveals a man-made object beneath the clothing; and if the one or more criteria are satisfied, displaying an image of the man-made object relative to a location on the person.

22. The method of claim 21, which includes inhibiting said displaying if the one or more criteria are not satisfied.

23. The method of claim 21, wherein said displaying includes showing the person with a gender-neutral representation.

24. The method of claim 21, wherein the man-made object is at least one of a weapon and contraband.

25. The method of claim 21, wherein the data sets each correspond to a spatial frequency representation of the respective one of the different image portions.

26. The method of claim 25, wherein said numerically processing includes:

performing a Fourier transform to provide spatial frequency data for each of the different image portions;

applying an image feature extraction filter to the spatial frequency data for each of the different image portions to provide a corresponding one of the data sets; and analyzing each of the data sets with a neural network, the one or more criteria including neural network weight values.

27. A system, comprising:

an array operable to interrogate a person with electromagnetic radiation at one or more frequencies in a range of about 200 MHz to about 1 THz; and one or more processors operable to establish data corresponding to an image of a surface beneath clothing of the person from one or more input signals from the array and generate a number of data sets each corresponding to a spatial frequency representation of a different portion of the image from the data, the one or more processors being further operable to analyze the data sets with a neural network to detect if the person is carrying a man-made object concealed by the clothing.

28. The system of claim 27, further comprising a display device responsive to said one or more processors to provide at least one image corresponding to the man-made object if the man-made object is detected.

29. The system of claim 27, further comprising a platform proximate to said array to support the person and a motor to move at least one of the array and the platform relative to another of the array and the platform to perform a security scan of the person at a security checkpoint.

30. The system of claim 27, wherein the processor is further operable to generate image data corresponding to a number of cylindrical images of the person.

31. The system of claim 27, further comprising:

means for processing portions of the data corresponding to portions of the image;

means for transforming the portions of the data to corresponding sets of spatial frequency image representation data; and means for extracting features from the sets of spatial frequency image representation data for analysis by the neural network, the data sets representing one or more features provided by said extracting means.

32. The system of claim 27, wherein the array is operable to provide the electromagnetic radiation at a plurality of different frequencies spanning at least a 10 GHz band.

33. An apparatus, comprising: a device carrying logic executable by one or more processors to analyze data corresponding to an image of a person obtained from electromagnetic radiation including one or more frequencies in a range of about 200 MHz to about 1 THz, the logic being further operable to generate a number of data sets each corresponding to a spatial frequency representation of a respective one of a number of different portions of the image, adaptively process each of the data sets relative to one or more criteria to determine if one or more of the different portions of the image show a man-made object concealed by clothing of the person, and provide one or more output signals to display at least a portion of the man-made object relative to a location on the person if the one or more criteria are satisfied.

34. The apparatus of claim 33, wherein the device is in the form of a processor-readable memory and the logic is in the form of a number of instructions stored in the memory.

35. The apparatus of claim 33, wherein the device includes one or more parts of a computer network and the logic is encoded in one or more signals for transmission over the computer network.

36. The apparatus of claim 33, wherein the logic is further operable to perform a Fourier transform operation with different portions of the data to correspondingly provide a number of sets of spatial frequency data.

37. The apparatus of claim 36, wherein the logic is further operable to apply an image feature filter to each of the sets of spatial frequency data to correspondingly provide the data sets.

38. The apparatus of claim 33, further comprising a display device responsive to the one or more output signals to provide an image of the man-made object at the location on a gender-neutral representation of the person.

39. The apparatus of claim 33, wherein the logic defines a neural network to adaptively process the data sets.

* * * * *